United States Patent [19]

McLeod

[11] Patent Number: 4,883,069
[45] Date of Patent: Nov. 28, 1989

[54] DYNAMIC JOINT MOTION ANALYSIS TECHNIQUE

[75] Inventor: Paul C. McLeod, Little Rock, Ark.

[73] Assignee: Physical Diagnostics, Inc., Conway, Ark.

[21] Appl. No.: 502,916

[22] Filed: Jun. 10, 1983

Related U.S. Application Data

[62] Division of Ser. No. 340,070, Sep. 21, 1981, abandoned, which is a division of Ser. No. 139,908, Mar. 31, 1980, Pat. No. 4,306,571.

[51] Int. Cl.⁴ .............................................. A61B 5/10
[52] U.S. Cl. .................................................. 128/782
[58] Field of Search ....................... 128/774, 779, 782; 33/174 D

[56] References Cited

PUBLICATIONS

Chao et al., ISA Trans., vol. 17, No. 1, 1978, pp. 13–19.
Chao et al., J. Biomed. Eng., vol. 102, No. 4, Nov. 1978, pp. 301–310.
Townsend et al., J. Biomech., vol. 10, No. 3, 1977, pp. 183–193.
Kettlekamp et al., "An Electrogoniometric Study of Knee Motion in Normal Gait," Journal of Bone and Joint Surgery, vol. 52—A, No. 4, Jun. 1970, pp. 775–790.

*Primary Examiner*—Max Hindenburg
*Assistant Examiner*—J. Hanley
*Attorney, Agent, or Firm*—Jim Zegeer, Esq.

[57] ABSTRACT

A three-plane goniometer or angle measuring apparatus includes three small potentiometers which are closely spaced together to measure rotation of the knee about three different axes. The unit is primarily mounted on a cuff on the outside of the thigh. The mounting assembly for the three plane goniometer includes a curved yoke where the ends of the yoke curve from the front to the rear, with the goniometer unit being held between the ends of the rearwardly extending arms of the yoke, so that accurate measurement may be maintained in all three planes even while the knee is bent to its extreme flexed position. Extending downwardly from the goniometer is a square rod which slidably engages a square hole in a nylon ball mounted in a two-axis gimbal, which is secured to a cuff strapped to the calf of the leg. Injuries may be diagnosed or characterized by comparing the pattern for one leg before injury with the pattern for that leg after injury or by comparing the pattern for one (healthy) leg with that for the other (injury) leg. The goniometer is mounted so that it may be readily reversed and used for both the right and left legs. Associated processing circuitry includes corresponding reversing circuits for conforming the plots for the right and left leg, and also includes special face marking circuitry. Comparative tests may be made for different types of footwear and athletic playing surfaces, and the torque which is produced may be compared to determine the preferred foot gear or playing surface.

2 Claims, 8 Drawing Sheets

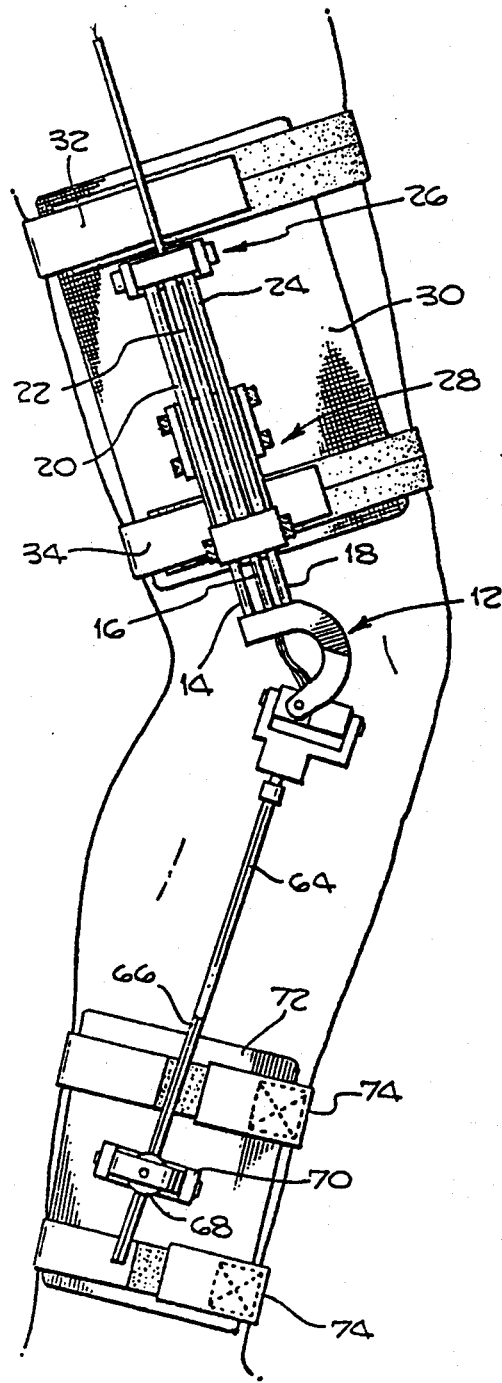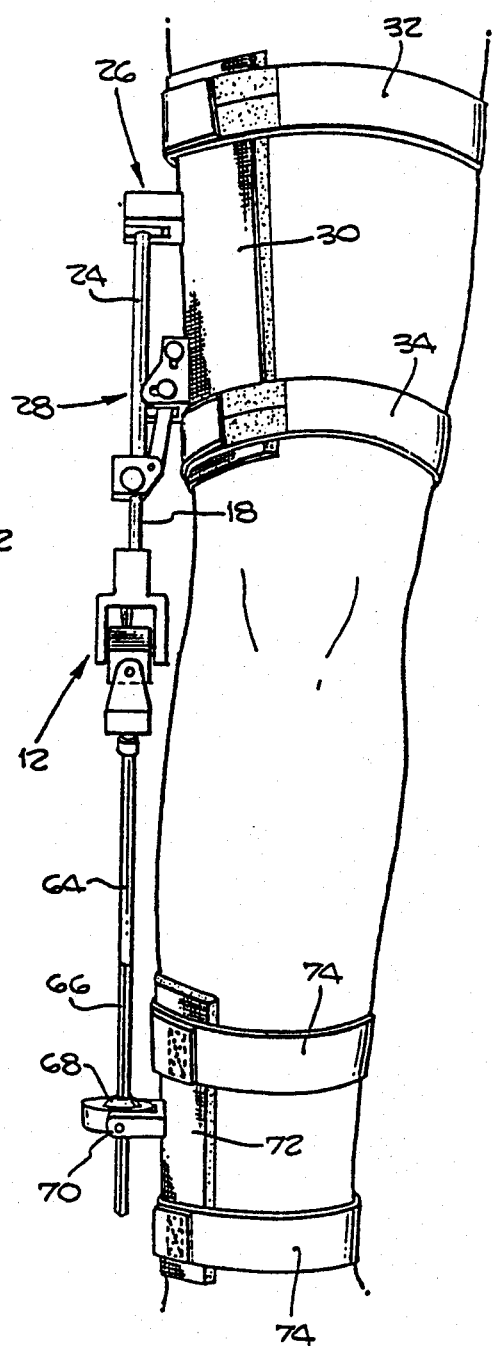

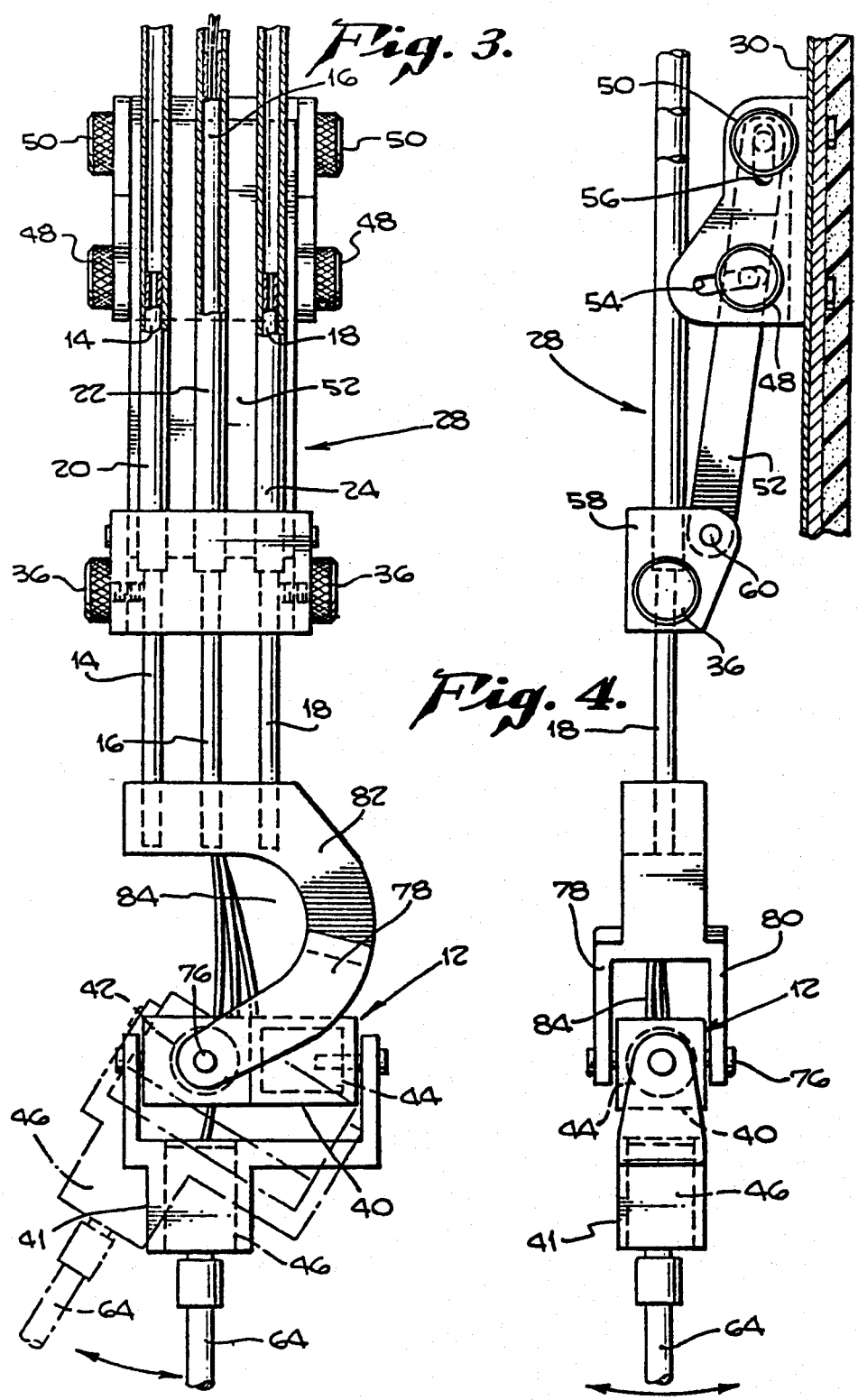

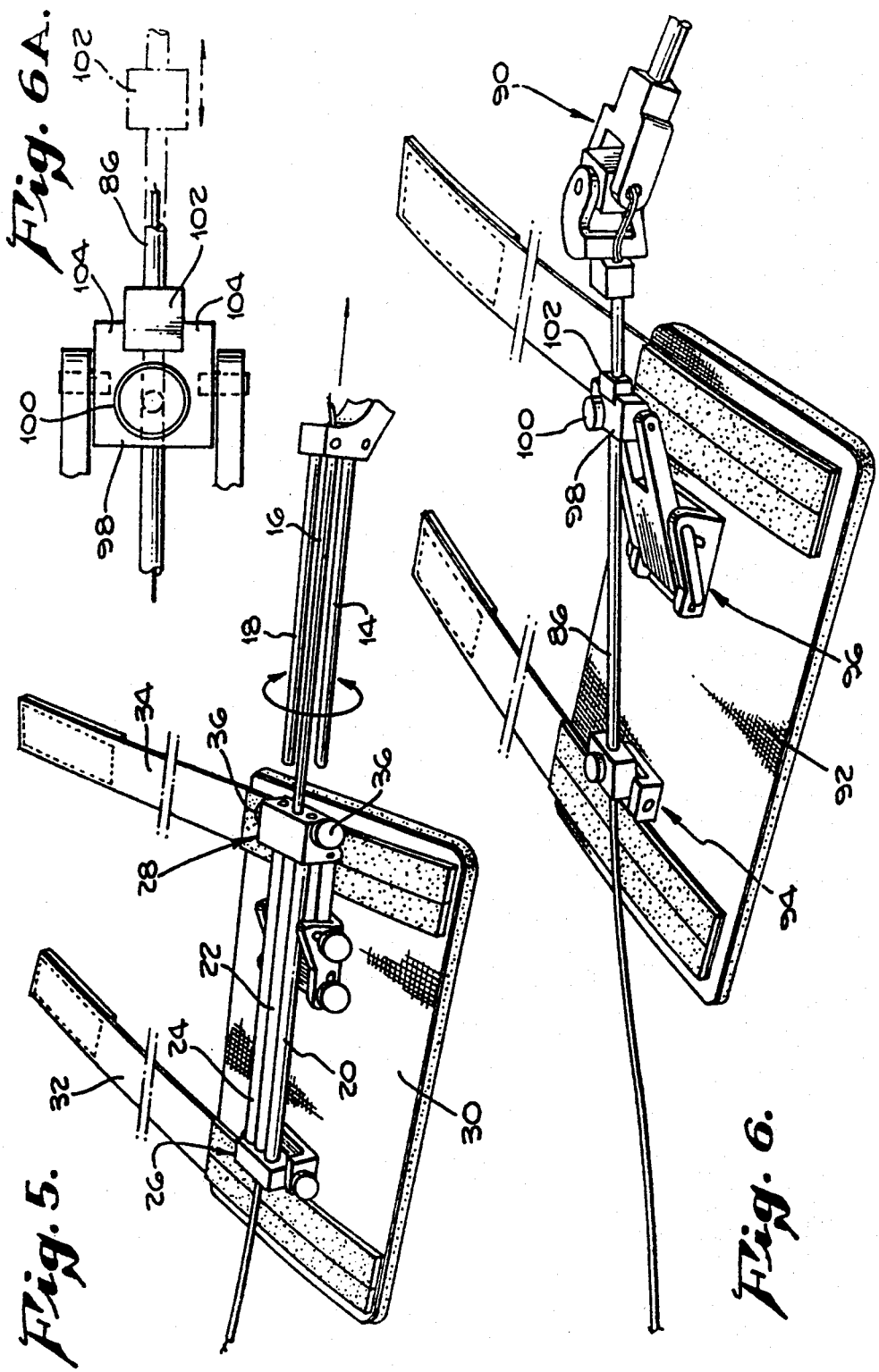

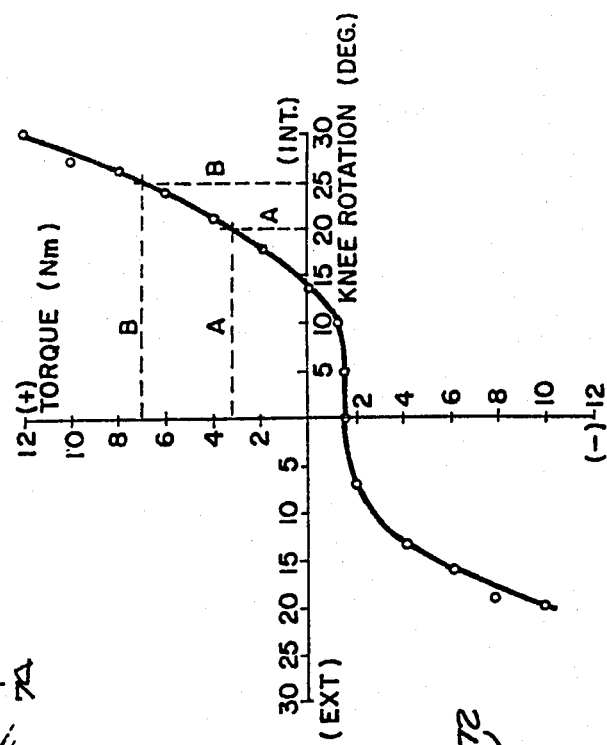
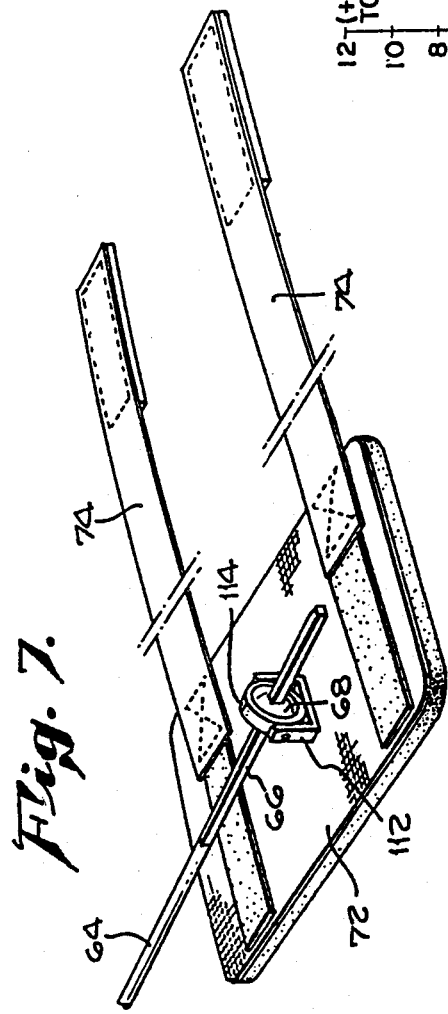
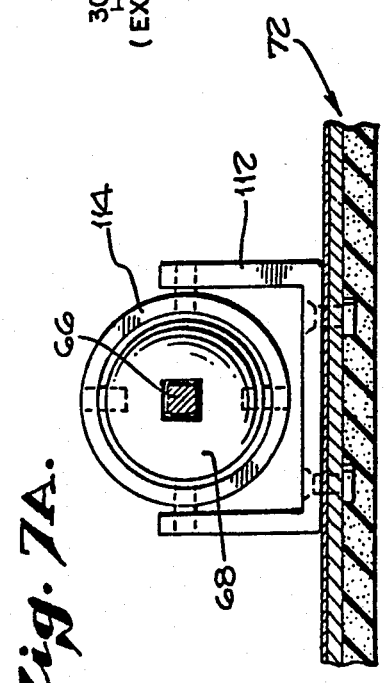

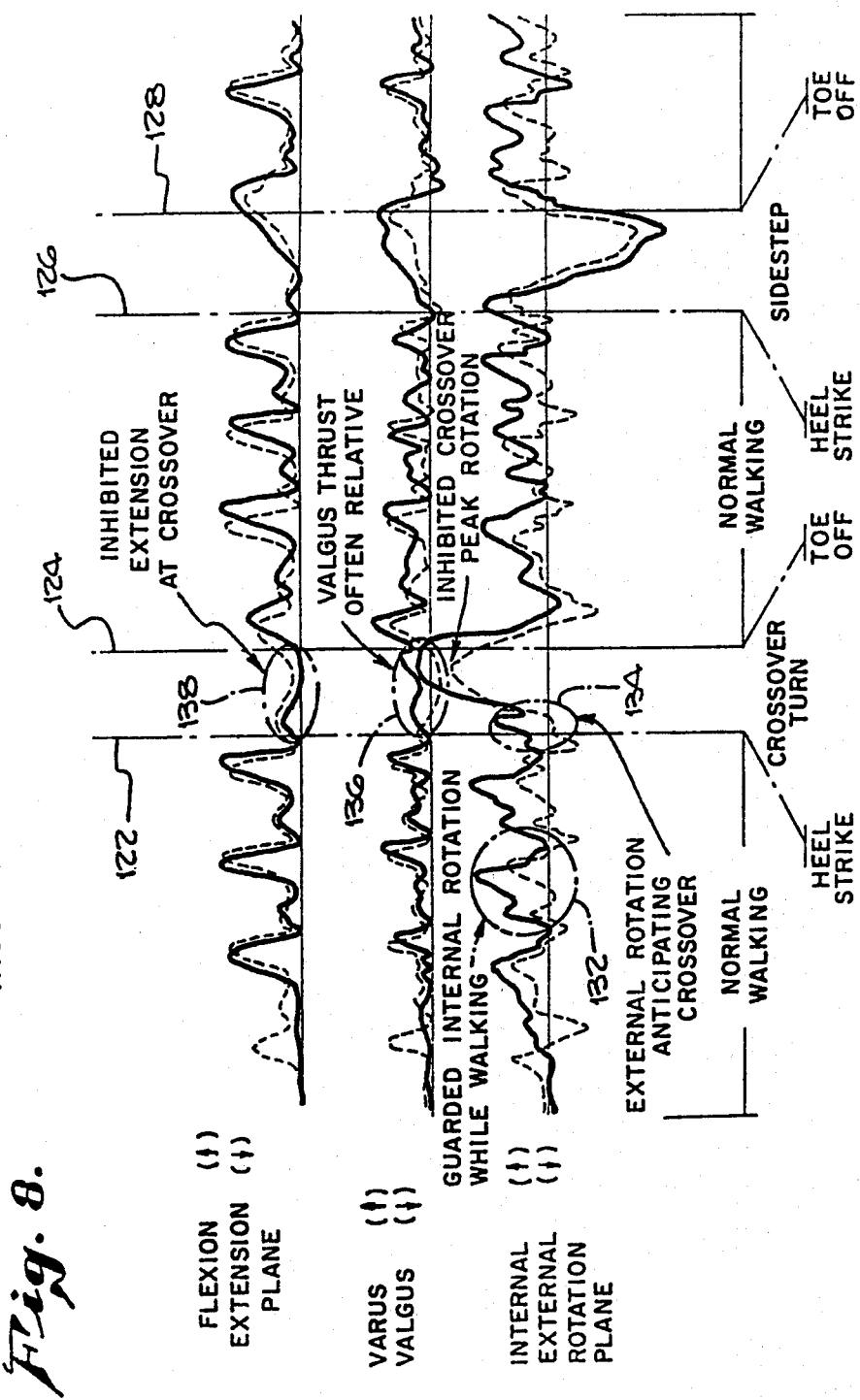

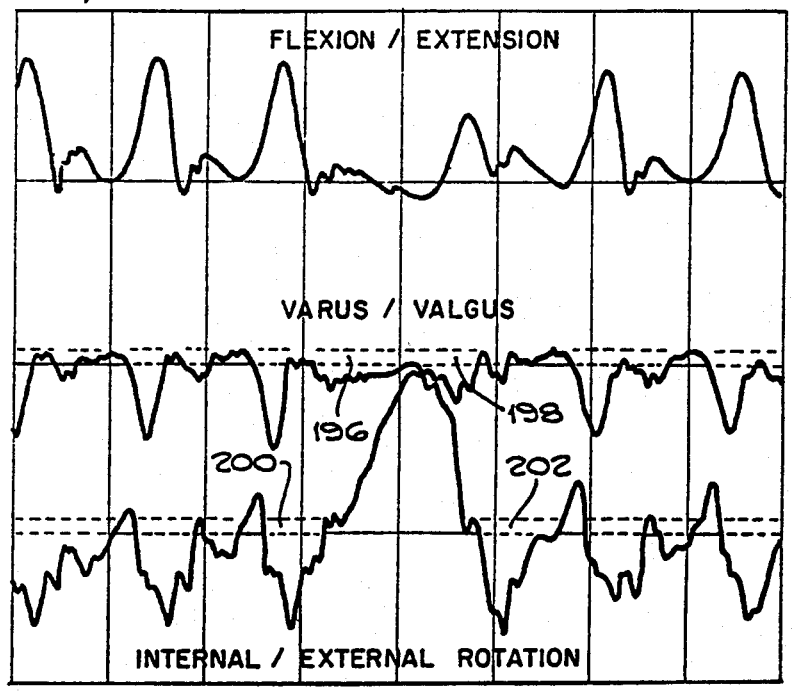
Fig. 11A.    NORMAL LEG, RIGHT
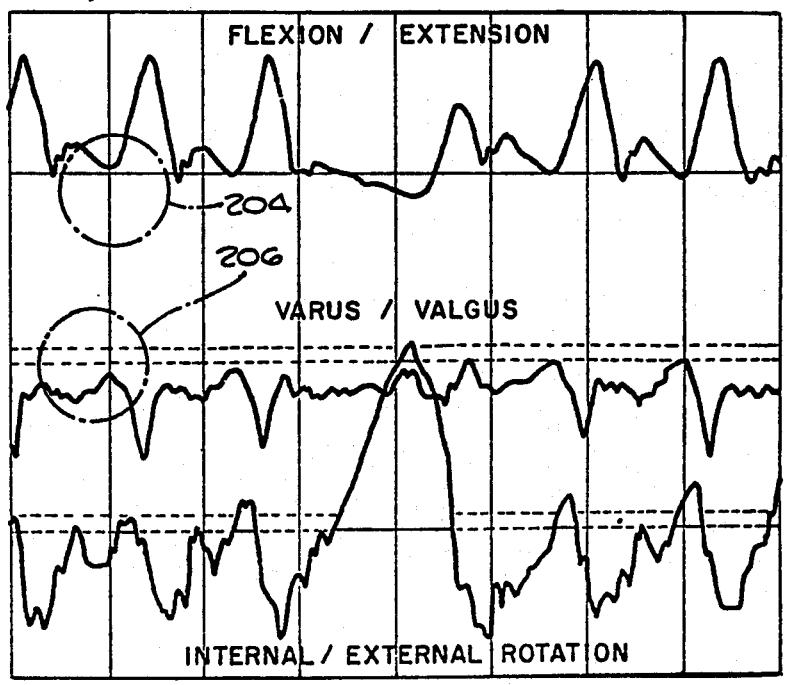
Fig. 11B.    INJURED LEG, LEFT

DYNAMIC JOINT MOTION ANALYSIS TECHNIQUE

This application is a division of my application Ser. No. 304,070, filed Sept. 21, 1981 for "Dynamic Joint Motion Analysis Technique", now abandoned, which, in turn, is a division of Ser. No. 139,908, filed Mar. 31, 1980, now U.S. Pat. No. 4,306,571, issued Dec. 22, 1981 and entitled "Dynamic Joint Motion Analysis Technique".

FIELD OF THE INVENTION

This invention relates to dynamic joint measuring techniques, and more particularly to arrangements for measuring and analyzing dynamic motion of the knee and other joints in three planes.

BACKGROUND OF THE INVENTION

It has previously been proposed to measure knee motion in all three planes, and a typical article disclosing such measurement is "An Electrogoniometric Study of Knee Motion in Normal Gait" by Donald B. Kettelkamp, M.D., et al., the Journal of Bone and Joint Surgery, Volume 52-A, No. 4, June 1970, pages 775 to 790.

In general, what the prior analyses show is that the human knee is a relatively complicated joint, and its motion is not limited to hinge-type action around a single transverse axis as might initially be expected of the knee joint. This front-to-back motion, which of course is the principal and major motion of the knee, is known as flexion-extension. Full extension of the knee is when the leg is stretched out and the knee joint locked; and full flexion of the knee occurs when the leg is bent so that the calf is firmly against the thigh. Studies of the knee show that in the course of normal walking, for example, the knee goes through two flexion-extension cycles during each complete walking step, with maximum extension occuring during the swing phase, and an additional extension occurring during the time when the foot is engaging the ground. In addition to the flexion-extension motion, the knee also bends toward and away from the centerline of the body. This inward or outward motion is known variously as abduction/adduction, or varus/valgus motion, with "abduction" and "varus" referring to outward movement of the knee, and "adduction" and "valgus" referring to inward movement of the knee. In the present specification, we will use the designation varus/valgus but some of the prior articles use the comparable terms abduction/adduction. In addition to the two types of rotation mentioned above, the knee also may rotate about the long axis of the leg. This rotation is referred to as internal/external rotation. In summary therefore, the three types of motion of the knee to which reference will be made in the present specification are (1) flexion/extension, (2) varus/valgus, referring to the inward or outward bending of the knee, and (3) internal/external rotation.

The apparatus which has been employed up to the present time has been relatively cumbersome and massive, and the measurements which have been obtained have been similarly somewhat qualitative and inconsistent.

Accordingly, objects of the present invention include the provision of a lighter weight three-axis goniometer which is capable of measurement of athletes performing rapid and extreme physical movements, and one which will provide accurate and reliable information under such arduous conditions.

Another object of the present invention is to provide for the diagnosis of knee injuries by comparing a pattern produced by one leg before injury with the pattern produced by that leg after injury or by comparing the pattern produced by one (healthy) leg with that produced by the other (injured) leg.

Still another object of the present invention is to determine the torque which is produced under successive different controlled test conditions, for the purpose of testing athletic equipment or environments, such as foot gear and playing surface qualities, by way of specific examples.

SUMMARY OF THE INVENTION

In accordance with one aspect of the present invention a lightweight three-axis goniometer is provided with arrangements for mounting it on the outside of the thigh of a user, and the goniometer is supported from the thigh by a yoke, which has its ends on which the goniometer is pivotally mounted extending to the rear, to preclude mechanical interference in the course of the measurement of the movement of the knee in all three planes, despite concurrent extreme angular movements of the knee. In addition, arrangements may be provided for reversing the mounting of the goniometer on the mounting support, so that the same unit may be first used on one leg and then on the other. In this connection, it may be noted that, with a normal healthy person, the characteristic angular movements of the knee in all three planes are very nearly the same for the left and right knees. Accordingly, when a person has one leg injured, by using the healthy leg as a control, and then measuring the injured knee, considerable diagnostic information may be obtained. Similar information may be obtained by measuring the same knee before and after injury.

In accordance with another aspect of the invention, the goniometer may be employed to indicate the torque applied to the leg by different athletic equipment conditions. For example, when a football player is playing on an artificial surface, the effect of using different types of football shoes with different cleat configurations or materials, for example, on an artificial turf can be measured in the course of negotiating a standardized course in a predetermined period of time. The resultant comparative tests indicating the extreme angular deviations for two sets of conditions may be compared, and equipment or playing surface selections may be made based on such comparisons. One direct application of this type of testing is the selection of shoes for athletes that will minimize stress to the knee while still providing adequate traction, such selection possibly varying as playing surface conditions vary. Another direct application of this type of testing is to fit individuals with shoes based upon their particular anatomy such that stress to the knee will be minimized while walking or running. Still another direct application of this type of testing is the selection of playing surfaces which consistently minimize stress to the knee.

In the data processing circuitry employed in the processing of signals from the goniometer, switches may be provided for the reversing of the varus/valgus and the internal/external rotation signals, as the goniometer is switched from the left leg to the right leg, or vice versa, so that the plots for the two legs will have the same configuration, and may be more readily compared. In addition, the electronic circuitry may include a trace identification pattern associated with one or more of the three output signals from the goniometer, and if desired, these signals may be interrupted as the associated signal shifts from positive to negative or vice versa.

Other mechanical features of the goniometer assembly include (1) the use of high strength, lightweight plastic such as Delrin for the unit, (2) locating the potentiometers very close together, so that the potentiometer subassembly is less in extent than two inches, for example, (3) the use of mounting assemblies for securing the goniometer unit to the upper leg mount which lock positively in either of two orientations which are 180 degrees displaced from one another for reversing purposes, and (4) the use of a sliding rod which extends through an element such as a nylon sphere, mounted in a two axis gimbal on the lower leg, all for the purpose of measuring internal/external rotation.

Other objects, features, and advantages of the present invention will become apparent from a consideration of the following detailed description and from the accompanying drawings.

BRIEF DESCRIPTION OF THE DRAWINGS

FIG. 1 is a side view of a three plane goniometer and mounting assembly mounted on the leg of a person being tested;

FIG. 2 is a front view of the arrangement of FIG. 1;

FIGS. 3 and 4 are mutually orthogonal views of the goniometer and the lower mounting assembly secured to the upper leg, and relating to the unit shown in FIGS. 1 and 2.

FIG. 5 shows the unit partially disassembled to permit reversing for use on the other leg;

FIG. 6 shows an alternative lighter weight embodiment in which only a single mounting tube is employed instead of the three tubes shown in the unit of FIGS. 1 through 5;

FIG. 6A is an enlarged view of one portion of the unit of FIG. 6;

FIG. 7 is a showing of a unit, including a gimbal subassembly, for securing to the lower leg;

FIG. 7A is an enlarged view of one portion of the unit of FIG. 7;

FIG. 8 is a plot comparing normal knee motion with knee motion in which one of the ligaments, the anterior cruciate ligament, is weak, or has been damaged;

FIG. 9 is a plot of torque versus internal/external knee rotation;

FIGS. 11A and 11B show the classic differences between a normal knee and a knee in which a lateral miniscus or other lateral compartment injury is present.

DETAILED DESCRIPTION

Figure 10A:
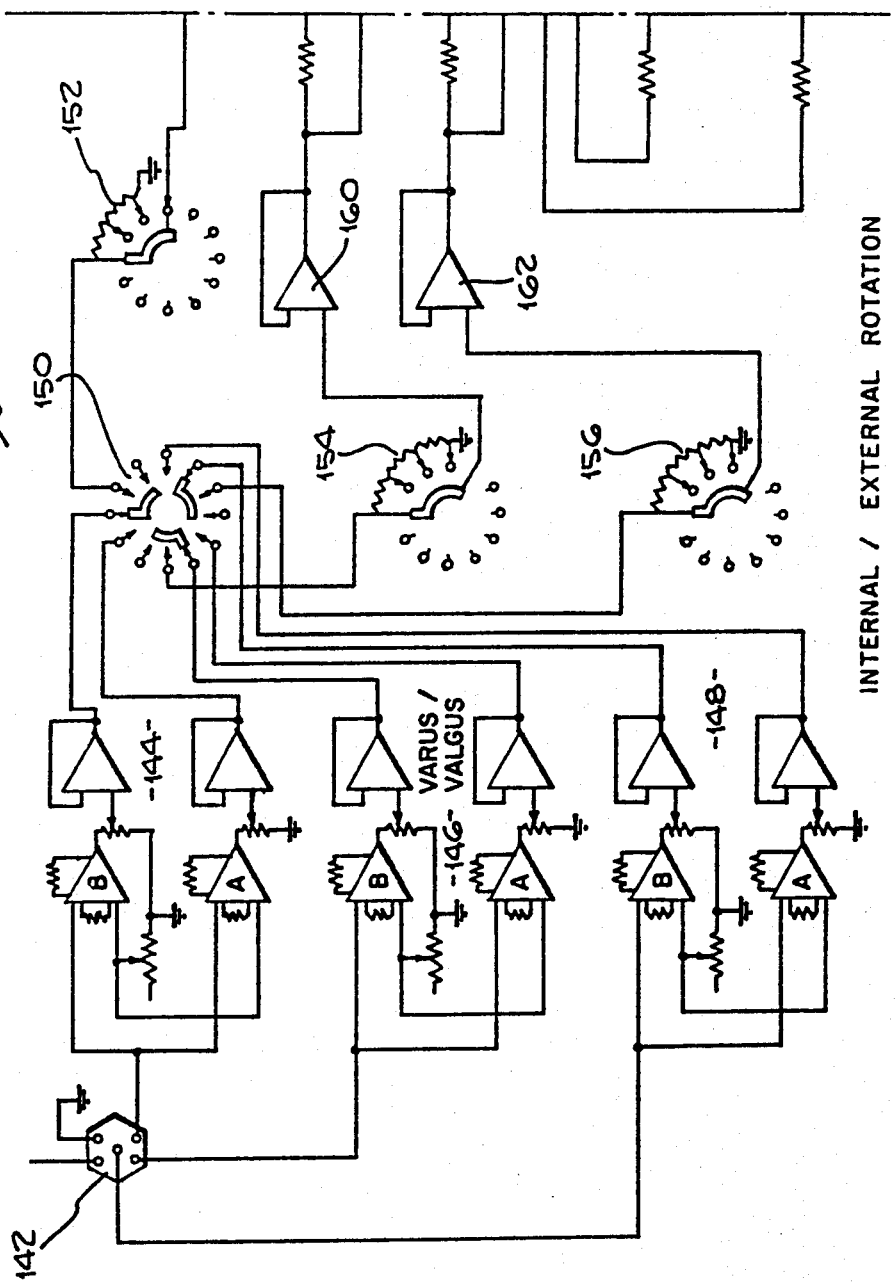
FIGS. 10A and 10B are two parts of the circuit diagram of the circuit for amplifying and recording the signals received from the goniometer units described hereinabove.

Referring more particularly to the drawings, FIG. 1 is a side view of the leg of a man with a three axis goniometer assembly 12 mounted near the knee. The goniometer assembly 12 is mounted from three tubes 14, 16 and 18 which slide into the three additional mounting tubes 20, 22 and 24. The tubes 20, 22 and 24 are mounted in two brackets 26 and 28, which are secured to a mounting pad 30, which is in turn mounted on the outer side of the man's thigh by adjustable straps 32 and 34 provided with Velcro or other suitable arrangements for securing the straps around the wearer's upper leg.

As indicated in FIGS. 3 and 4, the lower mounting unit 28 is adjustable to permit the goniometer assembly 12 to be moved closer or farther away from the knee, all depending on the musculature and the general configuration of the thigh relative to the knee, with the goal being to locate the goniometer assembly 12 as close as possible to the knee. The tubes 14, 16 and 18 are slidable within the tubes 20, 22 and 24, and are held in their desired position so that the goniometer assembly 12 is properly located relative to the knee by the knurled adjustment screws 36.

The central tube 16 is longer than the two outer tubes 14 and 18, so that, as shown in FIG. 5, when it is desired to reverse the position of the goniometer assembly 12 to mount it on the left leg, the knurled screws only have to be loosened, and tube 14 is first slid out of tube 20 and then, following rotation, it is slid back into tube 24 and tube 18 slid back into tube 20. Incidentally, the leads from the potentiometers 42, 44 and 46 which are included in the goniometer assembly 12 extend up through the central tubes 16 and 22.

Inward and outward adjustment of the goniometer assembly 12, toward and away from the knee, is accomplished by adjustments involving the pairs of knurled knobs 48 and 50 (see FIG. 4). A screw secured to one of the two knobs 48, is threaded into the other of the knobs 48, whereby the slanted and movable internal beam 52 may be shifted in its angle relative to the pad 30 as the shanks of the screws associated with knurled knobs 48 and 50 move in the slots 54 and 56. The lower tube supporting element 58 is pivotally secured to the plastic member 52 by pin 60, and is otherwise held in its proper alignment by the orientation of the tubes 20, 22 and 24 which are also pivotally mounted at their upper ends on the plastic element 26 (see FIGS. 1 and 2).

Extending downwardly from the potentiometer 46 is a metal rod 64 which has a lower end 66 which is of square or other non-circular configuration. The square rod 66 passes through and is slidable within a nylon sphere 68, which has a central rectangular opening and which is mounted in a two-axis gimbal arrangement 70 shown in FIGS. 7 and 7A, and which in turn is mounted on a cuff 72 secured to the lower leg by suitable straps 74 which are somewhat elastic and which are adjustable in the same manner as the straps 32 and 34 employed to secure the cuff 30 to the thigh.

The cuffs include a sheet aluminum alloy, which is approximately 0.032 inch thick. The sheet aluminum is covered with vinyl material on its exterior surface, and the cuffs are provided with a one-fourth inch thick foam rubber layer on their interior surfaces.

As best shown in FIGS. 3 and 4, the goniometer assembly 12 includes two potentiometer housings 40 and 41 which house the three precision potentiometers 42, 44 and 46 (potentiometers 42 and 44 in housing 40 and potentiometer 46 in housing 41). The potentiometer 42 is operated by a pin 76 which extends outwardly from the potentiometer 42 and is secured to the end of the yoke having the two rearwardly extending arms 78 and 80, said yoke constituting a first movable member. The potentiometer 42 measures flexion/extension, the normal major pivotal motion of the knee, and is capable of measuring up to 145 degrees. The cutaway configuration of the support member 82 with its substantial opening 84 provides for the varus/valgus motion as measured by potentiometer 44 as well as for internal/external rotation as measured by potentiometer 46, without mechanical interference, despite a full range of movement of the three potentiometers about the pin 76, square rod 64, via potentiometer 41, actuates housing 41 which constitutes a second movable member.

As discussed earlier, FIG. 5 shows the method of rotation of the goniometer assembly 12 relative to the mounting pad 30 and the associated bracket 28. Specifically, the knurled knobs 36 are loosened, the three tubes 14, 16 and 18 are slid downward until only the central tube 16 which carries the electrical conductors is in engagement, and the unit is rotated by 180 degrees so that tube 14 engages tube 24, and tube 18 engages tube 20 and the unit is then reassembled for the use on the left leg. Again, with the new orientation of the unit, and with the cuff 30 mounted on the left leg, the ends of the yoke members 78 and 80 will again be directed to the rear, and the unit will accommodate the full range of flexion/extension motion of the left leg. It may be noted in passing, that in the absence of arrangements for reversing the unit as it is shifted from the left leg to the right leg or vice versa, the potentiometer 42 for measuring flexion-extension would have different angular ranges for the right and left leg, and the curved yoke including legs 78,80 would not provide clearances for the extreme rotation about several axes simultaneously for both the right and the left leg. Accordingly, without reversibility, some decrease in sensitivity, and/or mechanical interference with extreme motion, is to be expected. Alternatively, a much more bulky and heavy unit would have to be employed.

FIGS. 6 and 6A show an alternative and somewhat lighter embodiment of the invention in which only one tube 86 slidable within the mounting bracket 94 and the lower pivoted plastic member 98 is used. The three axis goniometer 90 is similar in configuration to the unit 12 as employed in the arrangements of FIGS. 1 through 5, but is slightly smaller and lighter in weight. Again, it includes a yoke with rearwardly directed arms for increased mechanical clearance, and three potentiometers. The unit of FIG. 6 is very similar to that of FIGS. 1 through 5 and employs a cuff 92 with associated straps, and a similar upper mounting bracket 94 and a lower mounting bracket 96. The lower mounting bracket 96 is provided with similar arrangements for adjusting the height of the lower pivoted plastic member 98 which corresponds generally to the pivoted member 58 as shown in FIG. 4. The front bracket member 98 is provided with a knurled clamping nut 100 to hold the tube 86 in one of two orientations, which are 180 degrees displaced from one another. These two orientations are accomplished through the use of a rectangular plastic block 102 which is secured to the tube 86 and which is held in its proper orientation by the upper and lower protruding lips 104 extending downwardly from the block 98. With this arrangement, and with the block 102 being slightly wider than it is high, there are only two possible orientations with block 102 in engagement with member 98, one being for use on the right leg and the other for use on the left leg.

FIGS. 7 and 7A show the arrangements whereby internal/external rotation of the knee as measured at the lower leg rotates the shaft 64 and in turn rotates the potentiometer 46 or the corresponding potentiometer of the single tube arrangement of FIG. 6. As mentioned above, the lower end 66 of the shaft 64 has a non-circular or square configuration, and is journalled in the nylon ball 68 in order to permit the rod 64 to freely slide up and down relative to the element 68. Further, in order to permit changes in angle of the rod 64 relative to the cuff 72, a two-axis gimbal is provided which includes the U-shaped frame 112 which is secured to the cuff 72. Mounted in the U-shaped frame 112 is the gimbal ring 114, and it in turn mounts the ball 68 about an axis which is perpendicular to the base 112. With this arrangement, changes in alignment of the shaft 64 relative to the cuff 72 are readily permitted, but actual rotation of the lower portion of the leg is fully transmitted to the shaft 64 and result in changes in the output from potentiometer 46.

The plots of FIG. 8 represent the culmination of the use of the units as described hereinabove, together with the processing and recording circuitry to be discussed below. In FIG. 8, an injured knee is compared with a normal knee by switching the unit as described hereinabove from one leg to the other. Plots from the "control" or normal knee are shown in solid lines, while output plots from the injured knee are shown by dashed lines. In FIG. 8 the top graph represents flexion/extension, the middle graph represents varus/valgus movement, and the lowermost graph refers to internal/external rotation. The first portion, proceeding from left to right represents a normal walking pattern, the second portion between lines 122 and 124 represents a crossover turn, the next section between lines 124 and 126 is again normal walking while the space between lines 126 and 128 represents a sidestep, and this is followed again by normal walking.

In reviewing the normal knee plots as shown in the solid lines, it is noted that there are two maxima in leg flexion or bending which occur during each cycle of walking from one heel strike to the next heel strike, for example. One of these maxima occurs while the leg is swinging and the other smaller maxima or peak occurs while the foot is in engagement with the ground. A similar pattern, but with less angular extent is present with the varus/valgus characteristic and also with the internal/external rotation characteristic. Further, while the overall magnitude of the characteristics vary from person to person, the patterns are normally quite similar. In addition, and as mentioned above, for any particular individual, the left leg and the right leg normally produce patterns which have maxima and minima which are very nearly the same, and with the entire patterns being substantially the same, when there is no injury present.

If there were no injury present in the person being examined in FIG. 8, the solid line plot would be very nearly identical with the dashed line plot, or vice versa. However, in FIG. 8, there are in fact a number of significant departures of the injured knee characteristic as shown in dashed lines, as compared with the normal knee. These are emphasized by the circles 132, 134, 136 and 138. As indicated on the chart, the circle 132 indicates guarded internal rotation while walking; and all of the next three anomalies are involved in the cross-over turn which is accomplished between lines 122 and 124. Specifically, the encircled area 134 in the internal/external rotation characteristic shows external rotation anticipating a cross-over; the encircled area 136 shows a variation in the valgus thrust, and the encircled area 138 indicates inhibited extension during cross-over.

As may be appreciated from the foregoing discussion, the knee is by no means a simple hinge-type joint, but is relatively complex. More specifically, the lower end of the femur, or heavy upper leg bone, is provided with two rounded protruberances, and these seat in the upper end of the tibia, which is the larger, lower leg bone. Two ligaments extend at angles across the knee joint, with these two crossing ligaments being referred to as the anterior cruciate and posterior cruciate ligaments, the anterior cruciate extending across from the upper outer side of the knee to the lower inner side of the knee in front of the posterior cruciate which extends from the upper inner side of the knee across behind the anterior cruciate toward the lower outside of the knee.

The pattern of departure from normality indicated by FIG. 8 represents an anterior cruciate ligament insufficiency. As developed below, other injuries to the knee produce characteristic anomalies in the pattern of normal and injured knee movement when standardized procedures are undertaken of the type described hereinabove in connection with FIG. 8. These characteristic patterns can be a useful diagnostic tool to indicate the type of injury, or the compartment in which the injury is probably located. Incidentally, in many cases, following diagnosis by normal techniques, the method of analysis as described herein has resulted in an improved, changed or more complete diagnosis which was useful in directing the corrective surgery or other medical techniques.

Consideration will now be given to torque applied to the knee. Initially, it must be clearly understood that a three-plane or three-axis goniometer does not measure torque. However, because of the torque versus angular rotation characteristic of the normal knee, the magnitude of the angle of internal/external rotation is a good indicator of changes in knee torque, under different conditions.

FIG. 9 is a plot of the average value of torque required to produce angular rotation of the tibia for seven normal knees. While the absolute value of the individual points of this plot may differ with a different group of knees, the shape and slopes will be similar for most normal knees.

In the course of studying different types of athletic shoes, an athlete initially wearing shoe "A" performed a specific set of manuevers which is known to rotationally stress the knee a predetermined number of times such as 10 times. The results of these tests showed that the average value of maximum internal tibial rotation was 20 degrees, and reference to FIG. 9 shows that 20 degrees of internal rotation is produced by a torque of approximately 3 Nm (Newton-Meters) on the joint. Subsequently, using shoe "B", the athlete repeated the same maneuvers on the same surface for the same number of times. For shoe "B" the average value of maximum internal rotation was 25 degrees, and reference to FIG. 9 reveals that approximately 7 Nm of torque is required to produce 25 degrees of tibial rotation. Accordingly, shoe "B" apparently transmits 2½ times the torque to the knee as shoe "A" for the same activity. And serious consideration must be given as to whether shoe "B" may safely be used in view of the greatly increased torque which is produced. Of course, torque is only one factor to be considered, and the degree of control achieved by the athlete with the two shoes must obviously be considered and perhaps a suitable compromise shoe configuration selected.

It is also noted that the qualities of various playing surfaces may also be tested by repetitive activity on the different surfaces using a single pair of shoes on both surfaces, and a standardized series of maneuvers. Such tests could be useful in the design or selection of suitable natural substances or artificial "carpets" to be employed as coverings for athletic fields. It is also noted in passing that tiring of the athlete may be a factor; accordingly, the athlete should either rest between successive series under different conditions, or alternate tests, first using one set of conditions, then the other, and continuing successive alternations.

Still another specific example of how the goniometer readings may be used is the fitting of shoes to an individual such that stresses to the knee will be minimized. Because of differences in the physical make-up of individuals, some shoes create considerable stresses to the knee, while others will dampen such stresses. The inward or outward slant of a shoe sole has such effects depending on how an individual's foot normally contacts the ground. By having a person negotiate standard maneuvers wearing different shoes and comparing goniometer readings, the shoes that are best for that person from a knee stress standpoint can be found.

Still another specific example of how the goniometer readings may be used is the selection of shoes for athletes that will minimize knee stresses while providing adequate traction on varying playing surfaces. Most teams, such as football, soccer, baseball, etc., today play on a variety of surfaces depending on location and weather. One such surface for a given athlete with a given pair of shoes might create knee stresses of a relatively small magnitude, while another surface with the same athlete and shoes might create knee stresses of a dangerously high magnitude. By having the athlete perform standard maneuvers with different shoes on any given field and comparing goniometer readings, the shoes from that lot that are best in minimizing knee stresses while providing adequate traction, can be selected.

Figure 10B:
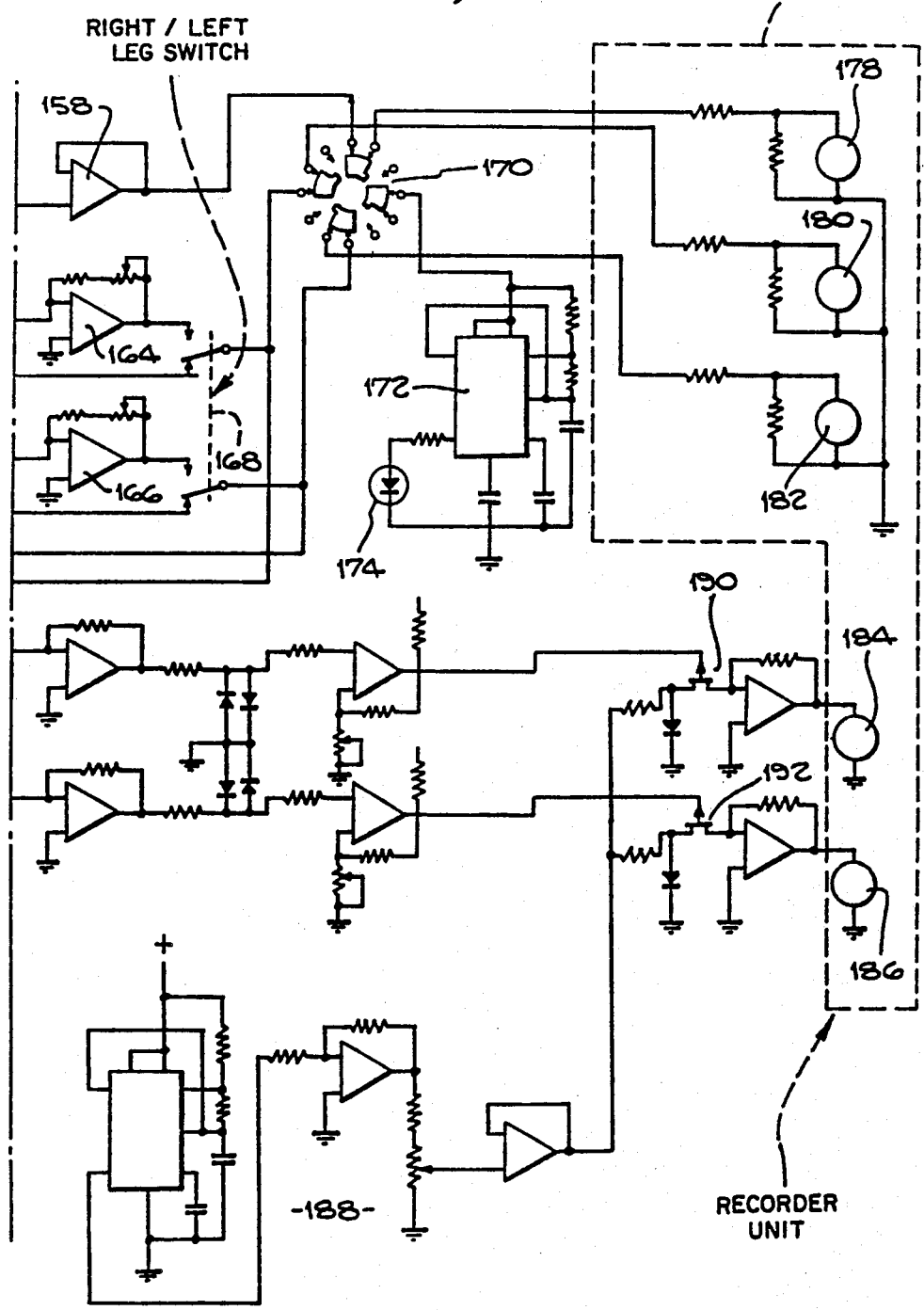

FIGS. 10A and 10B together form a circuit for processing the signals from the three axis goniometers described hereinabove. More particularly, the leads from the three potentiometers are connected through one of the tubes, and are brought through the tubes onto the wearer's body. In the case of routine walking tests, such as those described in connection with FIG. 8, long leads may be employed to connect to the connector block 142 as shown in FIG. 10A. Alternatively, in the event that more freedom of activity to conduct wider-ranging tests is required, simple telemetry arrangements could be employed to route the signals from the person wearing the goniometer assembly to the processing and recording equipment of FIGS. 10A and 10B. In all events, signals from the three axis goniometer are routed to the connector 142 and from this connector the flexion/extension signals are routed to channel 144, the varus/valgus signals are routed to channel 146, and the internal/external rotation signals are routed to channel 148.

There are two instrumentation amplifiers A and B associated with each of the channels 144, 146, and 148. The reason for these two instrumentation amplifiers involves the different resistor settings required to accommodate the different impedances provided by the three axis goniometer as shown in FIGS. 1 through 5, and that shown in FIG. 6. Accordingly, when a switch is made from one of the goniometers to the other, the switch 150 is actuated to select signals from either the "A" or the "B" set of instrumentation amplifiers. The sensitivity controlling potentiometers 152, 154 and 156 control the sensitivity for flexion/extension, varus/valgus and internal/external rotation, as the maximum values for these various parameters may vary from patient to patient. Immediately after the sensitivity controlling potentiometers 152, 154 and 156, are found the voltage follower circuits 158, 160 and 162, respectively. Associated with the varus/valgus and the internal/external rotation channels are the polarity reversing circuits 164 and 166, respectively. The switch 168 serves to reverse the polarity and it is actuated as the three axis goniometers are switched from one leg to the other of a patient, thereby facilitating comparison of plots made by the left and right legs.

The switch 170 is the galvanometer on-off switch. The circuitry associated with chip 172 is a warning signal which energizes the warning lamp 174 when the galvanometers are turned off, to avoid an attempted test cycle with a patient proceeding through the specified maneuvers when the galvanometers are turned off. A recorder unit is generally indicated by the dashed line block 176. Within the block 176 are shown a series of three galvanometers 178, 180 and 182 associated respectively with the three channels corresponding to the three outputs from the goniometers. The two additional galvanometers 184 and 186 provide marker signals for the varus/valgus and internal/external rotation channels, as shown in FIGS. 11A and 11B to be described below. More specifically, a low frequency signal in the order of 10 to 30 hertz is provided by any suitable oscillator 188. The field effect transistors 190 and 192 selectively block the oscillator signal from the galvanometers 184 and 186 when the corresponding signals pass through a predetermined level. This serves to uniquely identify the particular signals associated with that channel and avoid their confusion of traces associated with adjacent channels, despite some occasional overlap. This will be shown in greater detail in connection with FIGS. 11A and 11B. The input circuits to the field effect transistors 190 and 192 are comparison circuits which establish the levels at which the FET's will block the signals from oscillator 188.

Now, referring to FIGS. 11A and 11B, the upper trace in each case represents flexion/extension; the central trace represents varus/valgus; and the lower trace represents internal/external rotation, in accordance with the normal practice in displaying these features. In FIG. 11A, the signal from the oscillator 188 appears at 196 and 198, and is interrupted between these two data plots, indicating that the varus/valgus signal exceeded the predetermined level represented by the lowermost extreme of the plots 196 and 198. Similarly, the marker pattern designated by the reference numerals 200 and 202 associated with the flexion/extension characteristic in FIG. 11A, is interrupted when the characteristic exceeds a predetermined level.

The plots of FIG. 11A are the graphs from a healthy right leg. However, the plots of FIG. 11B represents an injured left leg, which includes a lateral meniscus tear. In this case, the internal/external rotation is relatively normal, but there are anomalies in the flexion/extension and in the varus/valgus characteristics. More specifically, the flexion/extension characteristic shows about 8 degrees lack of extension in late mid-stance as indicated by the circle 204; and in the varus/valgus characteristic as indicated at the circle 206, instead of a slight varus signal in mid-stance, we find a 4 degree relative valgus at this point. These indications are characteristic of a lateral meniscus tear.

One set of interrelated features of the present invention deserves recapitulation. This involves the asymmetric configuration of the goniometer and its supporting yokes, in combination with the arrangements for mechanically reversing the goniometer relative to the thigh mount and also the electrical circuit reversing arrangements. More particularly, the fact that the upper yoke from which the potentiometers are supported curves to the rear to permit measurement during full movement of the leg in all three planes, has previously been pointed out. Also, the corresponding need for reversing the orientation of the goniometer relative to the thigh mounting cuff has been mentioned, both with regard to the three tube embodiment and also relative to the single tube embodiment of the invention. In addition, in connection with the circuit diagrams, the linked reversing switches for the varus/valgus signal and for the internal/external rotation signal have been mentioned. The result of these arrangements involves the accommodation of full and vigorous maneuvers while the plots are being taken through the special asymmetric yoke configuration, the use of the identical unit for both the right and left legs through the mechanical reversing configuration, and finally, the normalization of the plots for both the right and the left leg by the use of the electrical reversing switches for the varus/valgus and for the internal/external rotation signals. The overall result achieved is a very high sensitivity lightweight unit of universal applicability.

Incidentally, it has been mentioned above that the goniometer assembly is made of lightweight plastic and is of relatively small configuration. In the description, the slightly larger three-tube unit of FIGS. 1 through 5 has been described, and in addition, the one tube unit of FIGS. 6 and 6A has also been discussed. With regard to their specific configuration and constructional features, these two units are both made of high strength, lightweight plastic, such as Delrin. The rotational axes of the two yokes which are included in each of the goniometer units cross at a single point, and this point is located as close as possible in alignment with the flexion/extension axis of rotation of the knee. To give an indication of the dimensions of the units, the overall height of the three-tube unit from the upper surface of the upper support member 82 (see FIG. 3) to the lower surface of the potentiometer housing 46 is approximately 3¼ inches, with the corresponding dimension for the one tube unit of FIGS. 6 and 6a being approximately 2.9 inches. In this regard, the distance from the axis of rotation of the upper yoke to its upper surface for the three tube unit is approximately 2 inches, while the corresponding dimension for the one tube unit is approximately 1.5 inches. Similarly, the distance from the centerline of rotation of the lower yoke to its lower surface is approximately 1⅜ inches for the three-tube unit and approximately 1.4 inches for the one tube unit. Concerning the spacing of the arms 78–80 making up the yoke for the three tube unit, the outer dimension is approximately 1¼ inches total width, and the space within the yoke is approximately 1 inch, with the yoke arms 78 and 80 being about ⅛ inch thick; and the outer and inner corresponding dimensions for the one tube unit of FIG. 6 are approximately 1.115 inches and 0.835 inch, respectively.

Concerning the dimensions of the plastic housing containing potentiometers 42 and 44, it has dimensions of approximately 1 inch by 1⅜ inches long by ⅝ inch thick for the three tube unit; and the corresponding dimensions for the one tube unit were approximately 0.835 inch, by 1 inch long by 0.6 inch thick. It is interesting to note that the actual size of the goniometer unit including the three potentiometers is only about 2-3/16 inches in height in the case of the three tube unit, and only approximately 1.8 inches in height for the single tube unit. In addition, the thickness in the direction extending outwardly from the knee is only about 1¼ inches across the yoke for the three tube unit and approximately 1.115 inches for the one tube unit. From the foregoing dimensions, the very small size of the actual goniometer unit carrying the three potentiometers is evident, as is the reduced thickness of the unit as aligned with the knee, so that the center of rotation may be located very close to the knee.

Incidentally, the potentiometers employed in the three tube unit were New England Instrument Company Part No. 55 FL1-120, each having a total resistance value of 10,000 ohms. The potentiometers used in the single tube unit were plastic film type potentiometers, which were made by the inventors for this particular application.

In conclusion, it is to be understood that the present invention is not limited to that precisely as described hereinabove. For example, the three axis goniometer could have minor mechanical and electrical changes without departing from the guiding principles indicated in connection with the embodiments of FIGS. 1 through 5, and those of FIGS. 6 and 6A; the electrical circuit and the methods described herein could be implemented by somewhat different arrangements than those specifically shown and described; and the principles disclosed herein are applicable to goniometer assemblies for measuring joints other than the knee. Accordingly, the present invention is not to be considered limited to that precisely as described hereinabove.

What is claimed is

1. In an apparatus for the study of the motion of a joint between first and second limb members, said apparatus having a multiple plane electrical goniometer with first and second movable input members, first securing means for securing said first movable input member and said multiple plane electrical goniometer to said first limb member, second securing means for securing said second movable input member to said second limb member whereby relative angular movements between said first and said second limb members are sensed by said multiple plane electrical goniometer and converted to electrical signals, the improvement wherein said first movable input member has a shape so as to preclude the interference of movements of said joint in extreme angular deviations by said apparatus, the further improvement comprising internal beam means between said first means securing said first movable input member to said first limb member and said first movable input member, and means for adjusting the angle of said internal beam means to adjust the position of said multiple plane goniometer relative to said joint depending upon the musculature and general configuration of said first limb member.

2. In a system for the electrogoniometric study of the knee comprising a multiple plane goniometer assembly having means for generating an electrical signal proportional to angular movement between the tibia and thigh bones about three axis normal to each other and having as the center thereof said knee, and one axis coaxial with said thigh bone and another of said axis coaxial with said tibia bone, and a third axis being transverse relative to the other two axes, respectively, means for mounting said multiple plane goniometer assembly adjacent the outside of said knee, said mounting means including an upper mounting assembly for mounting the upper portion of said assembly from the thigh, the improvement comprising, means for adjusting the upper mounting assembly to permit said multiple plane goniometer to be positioned closed to or further away from the knee depending upon the musculature and general configuration of the thigh relative to the knee and wherein said multiple plane goniometer assembly includes a curved yoke means having a substantial opening to provide for varus/valgus motion as well as internal/external rotation and preclude interference in the measurement by said multiple plane goniometer of the movement of the knee in all planes despite concurrent extreme angular movements between the thigh and lower leg in one of said planes, said yoke curving in a rearward direction relative to the front of said knee and means connecting a rearward end of said curved yoke means to said upper mounting assembly.

* * * * *